United States Patent

Robinson

[11] Patent Number: 5,968,500
[45] Date of Patent: Oct. 19, 1999

[54] TISSUE MOISTURIZING COMPOSITION AND METHOD

[75] Inventor: Joseph R. Robinson, Madison, Wis.

[73] Assignee: Columbia Laboratories, Inc., Aventura, Fla.

[21] Appl. No.: 08/950,835

[22] Filed: Oct. 15, 1997

Related U.S. Application Data

[63] Continuation of application No. 07/855,034, Apr. 30, 1992, abandoned, which is a continuation-in-part of application No. 07/429,755, Oct. 31, 1989, abandoned, and application No. 07/429,770, Oct. 31, 1989, abandoned.

[51] Int. Cl.$^6$ .............................. A61K 9/22; A61K 9/52
[52] U.S. Cl. ...................................... 424/78.08; 424/78.02
[58] Field of Search ............................. 424/78.08, 78.02

[56] References Cited

U.S. PATENT DOCUMENTS

| | | | |
|---|---|---|---|
| 2,923,692 | 2/1960 | Ackerman | 524/548 |
| 4,032,629 | 6/1977 | Osberghaus | 424/78 |
| 4,548,990 | 10/1985 | Mueller . | |
| 4,552,755 | 11/1985 | Rander | 514/938 |
| 4,615,697 | 10/1986 | Robinson | 604/890 |
| 4,863,725 | 9/1989 | Perkner et al. | 514/873 |
| 4,900,554 | 2/1990 | Yanagabashi . | |

FOREIGN PATENT DOCUMENTS

| | | |
|---|---|---|
| 61-72706 | 4/1986 | Japan . |
| 8900451 | 10/1989 | WIPO . |
| 8906964 | 10/1989 | WIPO . |

OTHER PUBLICATIONS

Chem Ag. 99:110774g.
Chemical Abstracts, vol. 99, No. 14, Oct. 1983, p. 343, abstract 110774g citing to RO, A, 75553 (Intreprinderea De Antibiotice) Jan. 30, 1981.

*Primary Examiner*—Peter F. Kulkosky
*Attorney, Agent, or Firm*—Fulbright & Jaworski, L.L.P.

[57] ABSTRACT

A composition and method of moisturizing mammalian membranous tissue is disclosed. The composition utilized in this method includes water, a bioadhesive polymer as the moisturizing agent, and preferably, a consistency-enhancing agent. The bioadhesive is a water-swellable, but water-insoluble, particulate, fibrous, cross-linked carboxy-functional polymer containing (a) a plurality of repeating units of which at least about 80 percent contain at least one carboxyl functionality, and (b) about 0.05 to about 1.5 percent cross-linking agent substantially free from polyalkenyl polyether. The consistency-enhancing agent, when present, is a water-soluble or -dispersible anionic or non-ionic polymer. The composition is contacted with the tissue to be moisturized, and that contact is maintained for a time period sufficient to moisturize the contacted area.

12 Claims, 3 Drawing Sheets

TISSUE MOISTURIZING COMPOSITION AND METHOD

This application is a continuation of application Ser. No. 07/855,034 filed Apr. 30, 1992, now abandoned which is a continuation-in-part of application Ser. No. 07/429,755, filed Oct. 31, 1989, now abandoned, and of application Ser. No. 07/429,770, filed Oct. 31, 1989, now abandoned.

DESCRIPTION

1. Technical Field

This invention relates to a composition and method for moisturizing of epithelial cells, and particularly a method and composition for moisturizing that includes water, a particular bioadhesive and, preferably, a consistency-enhancing agent. This invention also relates to a method of preparing the moisturizing composition.

2. Background Art

Several environmental and pathologic conditions produce drying or desiccation of membranous tissue of the mammalian body. These conditions produce dry mouth (xerostomia), dry eye (sicca conditions) and dry vaginal, dry nasal or dry rectal mucosa, and/or dry skin that are aesthetically unpleasing and/or irritating to the individuals having such conditions.

One method for moisturization of dry tissue uses an oily substance as the principal ingredient in the form of creams, lotions, gel or salves that are applied to the affected tissue in an attempt to prevent further dehydration of the tissue. They act by placing a water-impermeable hydrophobic barrier over the treated tissue. Petrolatum, mineral oil, lanolin and isopropyl myristate are examples of hydrophobic materials so used. These preparations are of limited usefulness over a prolonged period of time. In addition, they impart a greasy, sticky feel to the skin and stain clothing.

Another method for moisturization uses hydrophilic molecules which can attract water. Hydrophilic small molecules such as glycerin and glycerin/water mixtures, urea, and propylene glycol are known humectants said to be useful in moisturizing skin.

Several synthetic hydrophilic materials, which in the presence of water adhere to the skin and/or mucous membranes, have been used by themselves or in conjunction with one or more active or treating agents in various pathological conditions, but they have not been used as moisturizers, for dryness of epithelial cells such as those of the skin or mucosa. These hydrophilic materials are often referred to in the art as hydrogels.

Certain hydrophilic, carboxy-functional polymers, namely those containing carboxylic acid groupings, are known for use as carriers for treating agents. U.S. Pat. No. 4,615,697 discloses the preferred polymer polycarbophil used in this invention used with a treating agent. The hydrogel polymer carrier of U.S. Pat. No. 3,074,852, is said to be a polymer of U.S. Pat. No. 2,798,053. The exemplary cross-linked polymer is said to be CARBOPOL® 934. The polymer of particular interest in U.S. Pat. No. 3,074,852 is said to be in acid form, and is more particularly described in U.S. Pat. No. 2,909,462. That particularly described polymer is again reported to be the material sold as CARBOPOL® 934 by B. F. Goodrich Chemical Company.

U.S. Pat. No. 4,226,848 discloses a composition for adhering a pharmaceutical preparation to the mucosa of the oral or nasal cavities. An exemplary acrylic acid polymer disclosed therein is the lightly cross-linked acrylic acid-allyl sucrose copolymer available under the trademark CARBOPOL® 934 from B. F. Goodrich Chemical Co., which is said to form a high viscosity gel-like dispersion in water.

U.S. Pat. No. 4,548,990 discloses a controlled-release drug delivery composition whose cross-linked polymeric portion is prepared from monomers that include 50 to 99 percent of a water-insoluble monoolefinic monomer or mixture. The polymer is said to swell in ethanol and in water with a swelling ratio of 2:1 to 22:1.

A particularly useful polycarboxylic acid copolymer for therapeutic or cosmetic use is described in B. F. Goodrich Company European Patent Application No. 88112198.2, Publication No. 0 301532, the preferred polymer of U.S. Pat. No. 4,615,697 and possibly covering Carbopol 976. The fluffy, powdery acrylic acid polymer is prepared in a non-aqueous, non-organic solvent polymerization medium such as carbon dioxide. The polymer has about 0.1 to about 6 percent by weight cross-linking. The copolymer is substantially water-insoluble but water-swellable. A 0.2 weight percent dispersion in distilled water is said to have a mucilage viscosity of at lease 1000 cycles per second ("cps").

Hydrophilic, carboxy-functional. water-soluble polymers have been used in cosmetic formulations. U.S. Pat. No. 4,863,725 discloses a water-soluble copolymer of glycerol and methacrylic and, namely polyglycerol methacrylate. German Offenlegungsschrift 24 19 046 describes linear and cross-linked polymers containing carboxyl and aldehyde groups as cosmetic compositions. Japanese Patent Publication 61-72706 refers to a cross-linked polyacrylic acid mono- or di-hydroxypropyl acrylate polymer. PCT Application Ser. No. PCT/US89/00451, International Publication No. WO 89/06964 published Aug. 10, 1989, refers to a polycarboxylic acid opthalmic preparation of specified pH, viscosity and osmolality for use in an opthalmic composition.

None of the disclosures of the art discussed before teaches or suggests that a water-swellable but water-insoluble cross-linked bioadhesive polycarboxylic acid polymer such as polycarbophil or a similar polymer can be used especially at an acidic pH as a moisturizing agent in a composition for dry epithelial cells, such as those of the skin and mucosa as is disclosed hereinafter. However PCT/US 89/00451 does refer to a dry eye/tear substitute formulation comprising Carbopol 976 in water.

SUMMARY OF THE INVENTION

The present invention includes a composition and method for moisturizing epithelial cells. In accordance with this method, the epithelial cells are contacted with an effective moisturizing amount of an aqueous moisturizing composition that contains water, a moisturizing amount of a water-swellable but water-insoluble cross-linked bioadhesive polycarboxylic acid polymer and preferably, a thickening smoothing amount of a consistency-enhancing agent. The bioadhesive polymer is a water-swellable, but water-insoluble, particulate or fibrous, cross-linked carboxy-functional polymer. The polymer is used to contact the epithelial cells of a mammal such as a human.

The bioadhesive polymer preferably contains (a) a plurality of repeating units of which at least about 80 percent, and preferably at least about 90 percent, contain at least one carboxyl functionality, and (b) about 0.01 to about 6 percent, preferably about 0.01 to about 2 percent, more preferably about 0.05 to about 1.5 percent, and most preferably about 0.05 to about 1.0 percent, cross-linking agent that is substantially free from polyalkenyl polyether, based upon the weights of unpolymerized starting materials; i. e., repeating units and cross-linking agent. The consistency-enhancing agent is a water-dispersible and preferably a water-soluble, non-ionic or anionic polymer.

The bioadhesive polymer is water-insoluble, but water-swellable. A polymer that is both water-insoluble (less than 1 percent dissolves in water), generally can absorb about 40 to about 100 percent its weight in water, as contrasted with the water-soluble polymers which can absorb considerably in excess of 100 times their weight in water.

In preferred practice, the dry bioadhesive polymer is sized to pass through a 400 mesh sieve screen, U.S. Standard Sieve Series. It is also preferred that the bioadhesive particle be dispersed in a physiologically tolerable diluent, and particularly a liquid that includes water. The solution can also include other ingredients known for use in the liquids for application to the epithelium.

The present invention provides several advantages and benefits.

One advantage of the present invention is that its compositions are not noticeably irritating to the mucosa with which they are contacted.

Another advantage of the present invention is that the bioadhesive moisturizing polymer has an apparent acidic pH value and a relatively high buffering capacity that helps to maintain the acidic pH value of surface tissues.

The moisturizing effects of the present compositions can be relatively long lasting, for example 2–3 days, because of insolubility of the bioadhesive polymer.

Yet another benefit of the present invention is that its compositions can be fabricated with relative ease.

Still further benefits and advantages of the present invention will be apparent to those skilled in the art from the Detailed Description, Examples and claims that follow.

BRIEF DESCRIPTION OF THE DRAWINGS

In the figures forming a part of this disclosure.

DETAILED DESCRIPTION OF THE INVENTION

The present invention relates to a composition and method of moisturizing epithelial cells such as a mucous membrane area of the mouth (buccal cavity), eye, vagina and the like by administering that moisturizing composition to a host mammal. The compositions themselves are aqueous compositions that comprise a moisturizing effective amount of a bioadhesive and preferably, a water-soluble or water-dispersible, polymeric consistency-enhancing agent. They are distinguished from the invention of U.S. Pat. No. 4,615,697 and PCT/US89/00451 in that they lack a treating agent other than a relatively inert liquid such as water or are primarily for use with dry tissue conditions.

The bioadhesive of this invention is preferably water-insoluble but water-swelling. The term water-insoluble used here means that the bioadhesive (lacking water-soluble impurities) shows no appreciable viscosity in its acid form at about pH 3 to 5 in a concentration no greater than about 2 to about 3% by weight. The term water-swellable means that the preparation, although not water-soluble, absorbs an appreciable amount of water, typically about 60 to about 100 times its weight.

The moisturizing composition is designed for use on the epithelial cells, namely skin and mucous membranes (mucosa), of a mammal, such as that of a horse or a human, to which the composition adheres in the presence of a sufficient amount of water to swell the bioadhesive. The composition so adhered to epithelia moisturizes the contacted body area for relatively long periods of time. Such time periods are longer than the time of moisturization for a similar composition that does not include a bioadhesive as disclosed herein. Indeed, for moisturization of epithelia, the bioadhesive moisturizer can remain in place and active for a time period of 10 to about 20 hours; i.e., the turn-over time for mucin or tissue, to about two to three days.

A composition useful in this invention is substantially non-toxic to the animals in which or on which it is placed.

The method of the present invention utilizes a hydrogel composition that holds substantial quantities of water in contact with the epithelial area of a host mammal for extended periods of time. This composition functions additionally as a polyelectrolyte and restricts ion efflux from the contacted mucous membrane. Such ion efflux with the associated water can cause water to move out of tissues. Further, the moisturizing bioadhesive when swollen by an aqueous medium is itself a polyelectrolyte, and produces a Donnan equilibrium effect, resulting in the facilitation of ion influx into the contacted tissue. This composition is retained in contact with the epithelial tissue for extended periods of time as a result of the substantial bioadhesive, and mucoadhesive, properties of the cross-linked polymer.

The method of moisturizing of the present invention is effective for moisturizing several "dry" tissues such as dry eye, dry skin, dry vagina, dry nasal passages, dry rectal passage and dry mouth.

In accordance with this method of moisturizing, a composition containing water, a moisturizing effective amount of a moisturizing agent and preferably, a thickening-smoothing amount of a water-dispersible polymeric consistency-enhancing agent is provided, as described before.

The contact is carried out in the presence of sufficient water to swell the bioadhesive and cause the bioadhesive-containing composition to adhere to the area contacted. That contact is maintained for a period of time sufficient to moisturize the contacted epithelial cells, and adjoining tissues if desired.

The method of this invention lowers the local pH value. For example, over a five-day treatment period in which subjects received daily treatments of a composition of this invention, or another, commercial vaginal moisturizer free of a bioadhesive, a difference in vaginal pH value was noted of about 0.5 pH units or more between women receiving the two products. The vaginal pH value observed for women using a product of this invention was about 4.8, with a lowered pH value from the untreated value of about 5.6, being maintained for about 48 hours after treatment ended.

Common yeasts, fungi and other microbes that cause vaginal infections do not grow well at a pH value of 5 or below. As a consequence, the before-described moisturizing method also provides a method of inhibiting vaginal yeast and fungal infections.

Each of the hereinafter-described compositions can be administered in accordance with this method.

A composition of this invention can be administered by several means to provide the desired contact between the epithelial cells and the composition. For example, the composition can be applied by rubbing the composition over the area to be moisturized. The composition can be applied by spray, hand, forceps, suppository, plunger, douche or other suitable instrument. Where the conjunctival epithelia are to be contacted, the aqueous composition described hereinafter can be instilled into the precorneal pockets of the eyes. Where the buccal, nasal, anal and/or vaginal epithelia are to be contacted, the composition can be applied by spray, hand, forceps, suppository, douche or other suitable instrument.

The composition is left in place (contact maintained) for a time sufficient for moisturization of the contacted (treated) area to occur and thereby provide its cosmetic function to the mammal. In most circumstances, the administered composition is eliminated from the body by a natural bodily mechanism, such as by dispersion or erosion caused mechanically or by an aqueous body fluid such as vaginal secretions, or by washing. The bioadhesive moisturizing polymer-containing composition can also be lost by mechanical action at the site of contact, as by action of the eyelid on the eyeball or tongue in the buccal cavity. For mucosa, a bioadhesive moisturizing polymer adheres to the mucin that covers the membrane or to the membrane itself. Mucin is replaced (turns over) within about 10 to about 20 hours, usually about every 17 hours, and the adhered bioadhesive moisturizing polymer can be lost with the mucin.

The principal ingredient of the moisturizing composition of this invention is a bioadhesive polymer.

The active moisturizer comprises the bioadhesive polymer, water, and preferably the water-dispersible consistency-enhancing agent. Adjuvants or diluents can be present, as well as other ingredients that are known for use in moisturizing compositions.

This bioadhesive polymer comprises a water-swellable, but water-insoluble, particulate or fibrous, crosslinked carboxy-functional polymer that exhibits bioadhesion as discussed hereinafter. The polymer preferably contains (a) a plurality of repeating units of which at least about 80 percent contain at least one carboxyl functionality and (b) 0.01 to about 6, preferably about 0.01 to about 2, more preferably about 0.05 to about 1.5 percent cross-linking agent and preferably substantially free from polyalkenyl polyether, with the percentages being based upon the weights of unpolymerized repeating unit and cross-linking agent, respectively. Preferably, at least about 90 percent of the repeating units contain at least one carboxyl functionality, still more preferably, at least 95 percent of those repeating units contain at least one carboxyl functionality. Also in most preferred practice, the bioadhesive contains about 0.05 to about 2 percent by weight of polymerized crosslinking agent.

A bioadhesive can be broadly defined as a material that adheres to a live or freshly killed biological surface such as mucous membrane or skin tissue. "Bioadhesion", as used herein to define a useful bioadhesive moisturizing polymer, is assayed by the procedure described hereinafter in Example 2 of U.S. Pat. No. 4,615,697 that measures the force required to separate two layers of freshly excised rabbit stomach tissue that are adhered together by an adhesive.

Using the procedure of U.S. Pat. No. 4,615,697, a bioadhesive can be defined as a material that requires a force of at least about 50 dynes/cm$^2$ to separate two adhered, freshly excised pieces of rabbit stomach tissue, following the procedure of Example 2. More preferably, the force is at least about 380 dynes/cm$^2$. An average force observed for polycarbophil is about 1073 dynes/cm$^2$. Upper limits for forces required to separate the freshly excised rabbit tissue are presently unknown, but are believed to be at least about 2000 dynes/cm$^2$.

As noted previously, preferably at least about 80 percent of the repeating units of a preferred bioadhesive contain at least one carboxyl functionality in order to achieve the desired amount of water-swellability in the water-insoluble polymer. Monomers that provide these repeating units include monoethylenically unsaturated and include acrylic acid, methacrylic acid, fumaric acid, maleic acid, maleic anhydride which may be hydrolyzed into its acid form during or after polymerization, itaconic acid, crotonic acid, and the like. Each of these acids can be used alone or in combination with other such acids or with one or more pharmaceutically or cosmetically acceptable salts of those acids. Acrylic acid is a particularly preferred monomer for providing the carboxyl groupcontaining repeating units of the bioadhesive polymer.

A preferred bioadhesive polymer useful in this invention is cross-linked by a cross-linking agent as is known in the art. The cross-linking agent is preferably substantially free from polyalkenyl polyethers, and is particularly free from polyalkenyl polyethers such as polyallyl sucrose or polyallyl pentaerythritol containing an average of at least three allyl groups per molecule as are reportedly present in CARBOPOL® 934. Exemplary of useful cross-linking agents are divinylbenzene, N,N-diallylacrylamide, 3,4-dihydroxy-1,5-hexadiene, 2,5-dimethyl-1,5-hexadiene and the like.

The amount of cross-linking of the bioadhesive is of some import. When less than about 0.05 weight percent of an appropriate cross-linking agent is present, the bioadhesive tends to become water-soluble, or water-dispersible, thereby losing its desired water-insoluble, water-swellable, character that is important to the invention. When greater than about 1 or 2 percent cross-linking agent, depending on the polymer, is present for a divinylbenzene or dihydroxy or dimethyl-substituted hexadiene cross-linking agent, the water-swellability of the bioadhesive begins to decrease appreciably. Preferably, the cross-linking agent is present at about 0.05 to about 1 or 2 percent. However, the preferred range will vary inter alia with the nature of the polymer, the nature of the cross-linker and the degree of cross-linking. The cross-linking agent amounts refer to the percentages of those predecessor, unpolymerized monomers in the reaction mixture from which the bioadhesive is polymerized.

A bioadhesive polymer useful herein can thus be in part defined as a reaction product of the copolymerization of at least 80 weight percent monoethylenically unsaturated carboxy-functional monomer and about 0.01 to about 2.0 weight percent of a crosslinking agent free of polyalkenyl polyether. The remaining monomers that can be present to constitute 100 percent by weight of the monomers are discussed below.

In addition to the above two ingredients, the bioadhesive polymer can also include polymerized monoethylenically unsaturated repeating units such as $C_1$–$C_6$ alkyl esters of one or more of the abovedescribed acids such as hexyl acrylate, butyl methacrylate and methyl crotonate; hydroxyalkylene-functional esters of the above-described acids that contain a per molecule average of 1 to about 4 oxyalkylene groups containing 2-3 carbon atoms such as hydroxyethyl methacrylate, hydroxypropyl acrylate and 5 tetraethylene glycol monoacrylate; methacrylamide, acrylamide and their $C_1$–$C_4$ mono- and di-alkyl derivatives such as N-methyl acrylamide, N-butyl methacrylamide and N,N-dimethyl acrylamide; styrene; and the like as are known in the art as being copolymerizable with the above described carboxyl functionality-containing monomers and cross-linking agents. The bioadhesive polymers most preferably are prepared from only the monoethylenically unsaturated carboxy-functional monomer and the cross-linking agent.

A bioadhesive moisturizing polymer useful herein can be prepared by conventional polymerization techniques described in the literature. Exemplary preparations of useful bioadhesives are provided hereinafter and can also be found in U.S. Pat. No. 2,810,716 and U.S. Pat. No. 3,202,577.

A polymer of this invention can also be prepared as described in European Patent Application No. 88112198.2, published as 0 301 532 A2 on Feb. 1, 1989. In accordance with that disclosure, acrylic acid and a cross-linker are reacted in carbon dioxide as solvent in the presence of an appropriate free radical initiator at a temperature of about 45 degrees to about 65 degrees C. and at a pressure above the mixture critical point, e.g. about 1250 pounds per square inch at 45 degrees C. to provide a fine, fluffy polymer.

The bioadhesive useful herein is particulate or fibrous, and swellable in water, but is insoluble in water. Reference to the properties of the bioadhesive polymers of this invention as being swellable but insoluble in water means that the polymer can absorb water, typically about 1 to about 100 times its weight in water but is sufficiently insoluble to provide a measureable viscosity at pH 6.5 at a concentration of 0.2 percent by weight in water.

The bioadhesive polymers of this invention are swellable in water; i.e., the polymer particles sorb water (adsorb or absorb) and thereby become larger in size in the presence of water. The water used for that swelling, is typically that provided by the aqueous composition of the present invention or it can in part be that provided by the body of the treated animal, such as by moisture transpiration or secretion through the skin, by mucosal transpiration in secretions, such as saliva or vaginal mucosal secretions, or by secretion of tears in the eye. It is noted, however, that the latter bodily secretions are normally not present or are present in relatively small amounts that give rise to the need for the composition.

The size of the bioadhesive particles has an effect upon the compositions of this invention. It is apparent that the bioadhesive particles should not be so large that the composition cannot be administered without undue difficulty. Similarly, particles sized larger than those discussed below can sometimes cause pain and irritation when administered for ocular, buccal or vaginal use. In addition, it appears as though particles sized as discussed below provide improved function to the moisturizer composition as compared to particles that are larger in size; i.e., in the longest dimension.

Typically, at the maximum, a useful bioadhesive polymer is sized to pass through a sieve screen having a 400 mesh (U.S. Standard Sieve Series); i. e., a 38 micron opening. Preferably, the bioadhesive polymer particles are smaller still and are sized so that the longest dimension is about 20 microns. Most preferably, the particles have a number average size of about 2 microns to about 5 microns in the longest dimension. Particles of a desired size can be obtained, for example, by grinding, crushing or otherwise comminuting larger particles, as well as by direct polymerization.

Particles having a relatively small size have a greater surface area per unit weight, swell more rapidly, and appear to adhere better than do particles having a relatively large size, and thus, a relatively small size is preferred for the particles. Bioadhesion measurements discussed before and in Example 2 hereinafter are carried out for convenience using a bioadhesive sized to pass through a 30 mesh sieve screen and be retained on a 40 mesh sieve screen (U.S. Standard Sieve Series); i.e., 30/40 mesh size.

Bioadhesion has not been found to be a function of the molecular weight of the bioadhesive. Consequently, the bioadhesive can be of substantially any molecular weight, so long as its adhesion in the adhesion test described hereinafter is at least about 50 dynes/cm$^2$ and preferably about 380 dynes/cm$^2$.

As noted previously, the bioadhesives can be prepared by polymerization in an aqueous medium. In preferred practice, that aqueous medium is a saturated solution of an alkaline earth metal salt such as magnesium sulfate. The alkaline earth metal salt serves at least two functions. First, it increases the density of the polymerization medium so that the polymerized bioadhesive floats on the surface of the aqueous medium and can be easily removed therefrom. Second, the use of magnesium sulfate, in particular, reduces the swelling of the bioadhesive in the aqueous medium so that polymerization and recovery are facilitated.

Bioadhesives so prepared typically contain about 0.5 to about 1 percent of the alkaline earth metal ion after several water rinsings of the polymer. These polymers thus differ from those in which an alkaline earth metal hydroxide is used to neutralize the carboxyl groups as in calcium or magnesium polycarbophil.

Particularly preferred bioadhesives that are commercially available are those materials sold under the designation polycarbophil by A. H. Robins Co. of Richmond, Va., and CARBOPOL® "EX55" also known as CARBOPOL® 976 by B. F. Goodrich Chemical Co. of Cleveland, Ohio, the manufacturer of CARBOPOL® 934 that is also discussed herein. *The United States Pharmacopeia* (U.S.P.) 1980 ed., United States Pharmacopeial Convention, Inc., Rockville, Md., at page 638, indicates that polycarbophil is a polyacrylic acid cross-linked with divinyl glycol that has a residue on ignition of less than 4.0 percent and absorbs about 60 times it original weight in test B under *Absorbing power*. The 1985 edition of the U.S.P. lists only calcium polycarbophil that contains 18–22 percent calcium and is different from the material described in the 1980 edition.

The material designated as "EX55" from the B. F. Goodrich Co., above, has a specific gravity of about 1.4 and sorbs (absorbs and adsorbs) about 60 to about 100 times its weight of water. That sorption value is similar to the sorption capacity of natural mucin. In contrast, CARBOPOL® 934 is reported to sorb several hundred times its weigh of water. A useful bioadhesive is also a polyanionic polymer with a charge density similar to mucin.

Useful bioadhesive polymers of this invention were examined as to their densities, which are typically about 1.30–1.70 grams/cubic centimeter (g/cc), or a specific gravity of about 1.30–1.70. The cross-linking percentage was found to have a small effect upon the resulting density of illustrative, synthesized polymers as is shown in the Table below. Also shown in that Table in Column 11 of U.S. Pat. No. 4,615,697.

The bioadhesive moisturizing agent is present in the compositions of this invention in an amount that is sufficient to provide moisturization for a desired period of time for which the composition of this invention is to be administered, and such an amount is referred to herein as "an effective moisturizing amount". As is well known, effective amounts of agents vary with the particular agent employed, the condition being treated and the rate at which the composition containing the agent is eliminated from the body, as well as varying with the animal in which it is used. Consequently, effective amounts of moisturizing agents can not be defined for each agent.

Thus, an effective moisturizing amount is that amount, which in a composition of this invention, provides a sufficient amount of the moisturizing agent to provide the requisite moisturization on the body of the treated mammal for the desired period of time. An effective amount can therefore also be defined as a moisturizing amount.

A moisturizing composition utilized in the method of the present invention is designed to provide about 0.25 grams to about 15 grams (g) of bioadhesive per 100 milliliters (about 0.25 to about 15 weight percent) of the composition. More preferably, a bioadhesive polymer is present at about 2 to about 5 grams per 100 ml of composition (about 2 to about 5 weight percent).

The moisturizing water can be provided by the composition or by the contacted epithelia, or both. Thus, the bioadhesive moisturizing agent can be dispersed and pre-swollen in an aqueous medium prior to application, or can be applied dry and free of water or can be applied dispersed in a vehicle that contains enough water to partially hydrate the bioadhesive moisturizing agent particles.

In addition to water and the before-mentioned bioadhesive polymer, a composition of the present invention preferably contains a thickening-smoothing amount of a consistency-enhancing agent that is a water-soluble or water-dispersible polymer.

A consistency-enhancing agent useful herein possesses sufficient water-solubility or -dispersibility that even small amounts can radically alter the viscosity of an aqueous composition. Such materials can exhibit bioadhesion, but because of their solubility or dispersibility in aqueous media, they tend to be lost relative quickly from a composition and thereby do not provide the relatively long term moisturization that is provided by a before-discussed bioadhesive polymer.

For ease of expression, a consistency enhancing agent will generally be referred to herein as being water-dispersible.

Regardless of whether a consistency-enhancing agent is dispersed or truly dissolved, a composition of such an agent present at up to about 10 percent in deionized or distilled water forms a single phase to the naked eye at 20 degrees C., and once prepared does not exhibit separation when maintained at 20 degrees C. for 24 hours. Where the consistency-adjusting agent is an acid, cations such as sodium, potassium and ammonium ions that are utilized to disperse or dissolve the consistency-adjusting agent can also be present in the composition.

Exemplary consistency-enhancing agents include anionic (carboxyl group-containing) and non-ionic polymers such as those containing a plurality of carboxyl groups and those containing a plurality of $C_2$–$C_3$ hydroxyalkyl groups. Specific, preferred consistency-enhancing polymer agents include carboxymethyl cellulose, hydroxypropyl cellulose, hydroxyethyl starch derivatives, hydroxyethyl cellulose, gums such as tragacanth, hydroxyethylacrylate or methacrylate, polyacrylamide, and lightly cross-linked polyacrylic acid polymers like the before-described CARBOPOL® 934, which is particularly preferred. CARBOPOL® 934 is reportedly a polymer of acrylic acid that is cross-linked with a polyallyl sucrose (a polyalkenyl sucrose) containing an average of at least three allyl groups per molecule. The preferred consistency-enhancing agent polymers are thus seen to be derivatized polysaccharides and polyacrylic acids; i.e., amides and hydroxyethyl esters. Additional consistency enhancing polymer agents include polyvinyl pyrrolidone, polyvinyl alcohol and polyethylene oxide.

A consistency-enhancing agent functions in a composition described herein as its name implies; i.e., to enhance the consistency of the composition. That enhancement is in two areas: viscosity and texture.

As already noted, a consistency-enhancing agent useful herein is water-dispersible and a relatively small amount of such a material can greatly increase the viscosity of or thicken an aqueous composition. Inasmuch as the bioadhesive lends relatively poorly controlled viscosity-building effects to an aqueous composition, a composition containing only a bioadhesive moisturizing polymeric agent can be too thin and runny or too stiff for a particular purpose such as in a vaginal product.

When admixed in the amounts and under the conditions discussed hereinafter, a bioadhesive moisturizing polymer and a consistency-enhancing polymer combine to provide an appropriately thickened aqueous moisturizing composition.

A particularly unexpected effect of the admixture of a useful bioadhesive moisturizing polymer and a consistency-enhancing polymer agent is that the texture of the resulting thickened composition is made smoother than when a bioadhesive moisturizing polymer is utilized alone. Thus, an aqueous composition that contains only a bioadhesive moisturizing polymer can exhibit a stiff and almost gritty feel, and as such could be uncomfortable in a vaginal product particularly during intercourse.

On the other hand, the presence of a consistency-enhancing polymer agent unexpectedly smoothens the aqueous composition so that it exhibits substantially no stiffness or grittiness. That smoothening of texture also provides enhanced lubricity to the composition.

The use of a single amount of the consistency-enhancing polymer agent provides both the required thickening and smoothing. Thus, the amount of that material utilized is described as a thickening-smoothing amount. The consistency-enhancing agent can be a single polymer or mixture of polymers such as those discussed before.

The consistency-enhancing polymer agent is present in a thickening-smoothing amount, which, along with the other components that can be present in an aqueous composition preferably provides a gel-like consistency with a viscosity of the product of about 4,000 to about 40,000 cps at 25 degrees C., measured as discussed in Example 6. As is discussed in greater detail hereinafter, the viscosity of the composition is a function of several variables, each of which can be changed to alter or maintain a desired viscosity.

A typical composition can contain about 0.25 to about 10 weight percent of a consistency-enhancing agent polymer.

More particularly, an amount of about 0.5 weight percent to about 5 weight percent is utilized.

A greater amount of a consistency-enhancing agent is generally utilized with a smaller amount of bioadhesive polymer, and vice versa. For example, a composition at a pH value of 2.2–2.5 containing 0.25 weight percent polycarbophil as the bioadhesive requires about 8–10 weight percent CARBOPOL® 934 to achieve a viscosity appropriate for mechanical placement in the vagina.

The moisturizing water can be provided by the composition or by the contacted epithelial cells, or both, although typically, the water is provided by the composition. Thus, the bioadhesive moisturizing and preferably present consistency-enhancing agents can be admixed and preswollen in an aqueous medium prior to application, or can be applied admixed in an aqueos vehicle that contains enough water to partially hydrate the bioadhesive moisturizing agent particles and the consistency-enhancing agent.

A useful aqueous composition can have a room temperature-consistency of a barely pourable liquid to a gel, the latter being preferred, with the consistency being a function of relative amounts of water, bioadhesive moisturizing polymer, consistency-enhancing polymer agent (when present), osmoticity and the pH value of the composition formed. A relatively low amount of the polymers in a given amount of water produces a relatively thinner composition than does a greater amount of the polymers, with the pH value being held constant at both concentrations.

The $pK_a$ of a useful bioadhesive moisturizing polymer is about 3 to 4. As a consequence, where a composition is at a pH value of about 5 to 6 or greater, substantially all of the acidic protons are neutralized and the polymer-containing composition exhibits its thickest consistency for that concentration. On the other hand, at pH values such as 2, below the polymer's $pK_a$ value, the composition is relatively thinner, for a given concentration.

The $pK_a$ values for the carboxylic acid-containing consistency-enhancing agents such as the particularly preferred CARBOPOL® 934 are similar to that of a bioadhesive polymer. As a consequence, use of a composition at a pH value of about 5 or greater provides the thickest composition, whereas use of a pH value of about 2 provides the thinnest composition, for a given concentration of consistency-enhancing agent and all other components being held constant. Non-ionic consistency-enhancing agents change their viscosity and that of the composition less over a range of pH values than do anionic materials.

In addition, osmoticity of a composition can also play a role in the viscosity of the composition. Typically, higher solute concentrations decrease the viscosity of a composition when the amounts of bioadhesive polymer, consistency-enhancing polymer (when present), water and the pH value are kept constant. Thus, the viscosity of a before-discussed composition having a pH value in excess of 5 can be reduced from that of a ringing gel to a pourable liquid by increasing the osmoticity of the composition.

An isotonic product has an osmoticity of about 280 to about 320 mOsM, and such an osmoticity is useful herein. The osmoticity of a moisturizing composition can be as high as about 450 to about 500 mOsM.

Pharmaceutically acceptable electrolytes and non-electrolytes (collectively referred to as solutes) are used for adjusting osmoticity and viscosity of a useful composition. Exemplary pharmaceutically acceptable electrolytes include sodium chloride, potassium chloride, sodium phosphate, potassium phosphate, sodium and potassium sulfates, and sodium and potassium bicarbonates. Exemplary pharmaceutically acceptable non-electrolytes include glycerin, sugars such as glucose and sucrose, sorbitol and urea. Thus, those solutes that are well known for adjusting osmolarity or osmolality are useful herein.

Osmoticity of a given composition is a measured value that is obtained using a vapor phase osmometer.

Thus, a composition containing a bioadhesive moisturizing polymer with or without a carboxy group containing consistency-enhancing polymer agent at or near the high end of the before-discussed concentrations and at a pH value of about 5 or greater exhibits more gel-like properties. Such compositions can, nevertheless, be extruded in the form of drops from an eye dropper, particularly where sufficient electrolyte or other solute is present to raise the osmoticity to near about 450 mOsM. Conversely, a composition at or near the low end of the before-discussed concentrations and at a pH value below about 3 typically behaves as a barely pourable liquid, unless a large amount of bioadhesive polymer is present.

In specific examples, a composition for vaginal moisturization can exhibit a viscosity of about 4,000 to about 40,000 cps at 25 degrees C., whereas a composition for buccal moisturization can exhibit a viscosity of about 1 to about 4,000 cps at 25 degrees C. The thicker compositions typically exhibit non-Newtonian flow characteristics. The viscosity of such solutions is therefore measured with a viscometer that is especially designed for such compositions. The viscometer utilized for the viscosity measurements discussed herein is a commercially available Haake ROTO-VISCO Model RV-12, available from Haake, Inc., 244 Saddle Brook Road, Saddle Brook, N.J. 07662. The machine utilized an SV cup and an SVII rotor for determining viscosity in centipoises (cps) at shear rates of 1–8 revolutions per minute (rpm) and at a temperature of 25 degrees C.

With these extremes of consistency in mind, a skilled worker can readily formulate a moisturizing composition having a desired consistency. It should also be understood that the pH value of a moisturizing composition can change once the composition is contacted with the epithelial tissues as a result of the local pH value of the area to which the composition is applied.

The moisturizing composition is applied to the epithelia in an amount sufficient to form a layer of hydrated bioadhesive particles that is substantially continuous over the applied surface. Typically, that layer is several particles thick. In terms of the dry bioadhesive moisturizing agent, the bioadhesive moisturizing agent is applied in an amount of about 1 to about 50 milligrams (mg) per square centimeter (cm2) of contacted epithelial cells. Application to the epithelia can be and preferably is in excess of that needed to provide moisturization.

The amount applied is also a function of the location of the application. For example, application to the eye requires a relatively small amount of total moisturizing composition due to possible discomfort that can arise when any foreign material is in the eye. Conversely, application to the skin and vaginal epithelia can be in excess of that needed to provide moisturization.

For example, about 0.025 to about 1.0 $mg/cm^2$ of moisturizing polymer (about 25 to about 50 microliters of a composition containing about 1 to about 3 weight percent of the polymer) are used for eye moisturizing compositions, whereas about 10 to about 50 mg/cm2 of moisturizing polymer are used for moisturizing skin.

For application to the buccal, nasal, rectal and vaginal epithelia, it is more convenient to refer to the amount of bioadhesive moisturizing polymer applied in terms of the total weight of the polymer applied. Thus, for the buccal epithelia, a composition containing about 0.25 to about 5 weight percent of the bioadhesive moisturizing polymer is applied. For the vaginal epithelia in particular, the amount of composition is about 1 to about 5 grams of a composition containing about 0.25 to about 3 weight percent of the bioadhesive polymer. This latter amount is in excess of that needed for moisturization, but the excess is useful in providing lubrication during sexual intercourse. Broadly, then, a liquid composition contains about 0.25 to about 5 weight percent bioadhesive polymer or moisturizing agent.

In addition to the bioadhesive polymer moisturizing agent and consistency-enhancing agent, a composition useful in this invention can also contain one or more pharmaceutically or cosmetically acceptable additives that are referred to herein as adjuvants that assist in providing shelf life and customer acceptance of a moisturizing product. Exemplary adjuvants include preservatives, astringents, skin toners, skin conditioning agents, skin feel enhancers, emollients, lubricating oils, emulsifying agents, humectants, coloring agents, and odor providing agents (odorants).

Typical preservatives known for use with moisturizers include alcohol, ascorbyl palmitate. benzoic acid, butylated hydroxyanisole, butylated hydroxytoluene, chlorobutanol, ethylenediamine, ethylparaben, ethyl vanillin, glycerin, methylparaben, monothioglycerol, phenol, phenylethyl alcohol, phenylmercuric nitrate, propylparaben, sassafras oil, sodium benzoate, sodium formaldehyde sulfoxylate, sodium metabisulfite, sorbic acid, sulfur dioxide, maleic acid, and propyl gallate. Obviously, to the extent any of the foregoing preservatives are irritating to sensitive tissue, less irritating preservatives should be chosen.

Typical astringents known for use with moisturizers are (1) the salts of aluminum, zinc, manganese, iron, and bismuth, (2) certain other salts that contain these metals (such as permanganates) and (3) tannins or related polyphenolic compounds.

Typical emollients known for use with moisturizers are bland, fatty or oleaginous substances used to soften, make more pliable, the skin through penetration of the emollient into the surface layers. Typical emollients known for use include castor oil, sulfated castor oil, cocoa butter, coconut oil, cold cream, corn oil, cottonseed oil, rosewater ointment (also known as cold cream), combinations of white wax and white petrolatum, combinations of sodium lauryl sulfate, propelyne glycol and stearyl alcohol, sesame oil, theobroma oil, myristyl alcohol and shark liver oil.

Typical lubricating agents or oils known for use with moisturizers are petrolatum, white or yellow wax, cocoa butter, oleic acid, olive oil, jojoba oil, paraffin, starch glycerite, lanolin, paraffin, hydrophilic petrolatum, mineral oil, cetyl alcohol, glyceryl monostearate, lanolin, stearic acid, polyethylene glycols, polyoxyl 40 stearate, polysorbate, cholesterol and higher molecular weight lipids.

Emollients and lubricants provide skin-care products with the appropriate slip, tactile feel and rub-in properties to enhance the ease of usage and to encourage the consumer to use the product more liberally and more frequently. Certain quantiary compounds allow substannces like petrolateum to be combined with glycerine and in personal-care products without feeling greasy. The petrolateum-glycerine combination is especially effective in alleviating dry skin.

Typical emulsifying agents known for use with moisturizers are sodium alginate, carbomer, carboxymethylcellulose sodium, carrageenan, gelatin, hydroxyethyl cellulose, hydroxypropyl cellulose, hydroxypropyl methylcellulose, octoxynol 9, oleyl alcohol, polyvinyl alcohol, povidone, sodium lauryl sulfate, sorbitan esters, stearyl alcohol, tragacanth, and xanthan gum. Emulsifying agents are used to produce oil-in-water emulsions and can be classified into three types: monomolecular, multimolecular and solid particle. Known monomolecular emulsifying agents include potassium laurate, polyoxyethylene sorbitan monooleate. Multimolecular emulsifying agents include acacia and gelatin. Solid particle emulsifying agents include bentonite, graphite and magnesium hydroxide. Emulsifying agents can also be classified chemically into inionic, cationic and nonionic.

Typical humectants known for use with moisturizing agents are glycerin, propylene glycol, pyrrolidone carboxylic acid, sodium lactate, urea, and certain natural lipid mixtures. Other known humectants include certain proteins, gelatin, hyaluronic acid, vitamins and some natural ingredients. Some of the protein used are collagen, hyaluronic acid, elastin, placental proteins and proteins from epidermal tissues of mammals are also used. In general humectants act by penetrating into the stratum corneum and increasing the amount of moisture of that is held in close association with the stratum corneum lipids or proteins.

The preparations are rendered sterile by autoclaving at elevated at temperatures and pressures for a sufficient level and for a sufficient time to kill all bacterial contaminants or they are prepared under aseptic conditions.

The preparation is rendered pyrogen-free by the use of pyrogen-free water which is available from commercial laboratories.

The phrases such as "pharmaceutically acceptable", "cosmetically acceptable" or "physiologically tolerable" are used herein to mean that the material so described can be used for treatments in or on humans or other mammals without causing ill effects, such as toxicity, blistering or whitening of mucosa or skin tissues, and that those materials are not themselves bioadhesive moisturizing agents, as those words are used herein. Exemplary adjuvants can be found in Chapter 67 of *Remington's Pharmaceutical Science*, 16th ed., Osol, et al. eds, Mack Publishing Company, Easton, Pa. (1980), as well as in Chapter 84 of the Seventeenth Edition thereof.

It is noted that the above-mentioned adjuvants can be present in an amount that is greater than the bioadhesive polymer. Even though such can be the case, the adjuvants do not provide the moisturization of the composition, but rather provide emulsification or lubricity or the like, and typically assist in application of the compositions. This is the case where a compound such as glycerin or sorbitol that is a known humectant is present since such materials are water soluble, non-bioadhesives that are typically lost with perspiration or the like. Lubricating oils and emulsifying agents provide lubricity to a composition for sexual intercourse.

A moisturizing composition useful herein can be applied to contact the epithelia as a dry powder, an aqueous suspension or a non-aqueous suspension. That application can be in the form of a spray of the powder or a suspension, to drops, to a composition having a cream or gel-like consistency.

In one embodiment, the dry bioadhesive moisturizing polymer is swollen in an aqueous medium at a desired pH value, and then applied to contact the desired tissue such as the eye. The word "dry" is used herein in relation to a bioadhesive moisturizing polymer to mean that the polymer does not adhere when touched with a finger within a rubber glove, and is substantially unswollen.

A bioadhesive can also be employed with suppositories for rectal or vaginal administration, in which case the bioadhesive polymer is dispersed therein. A thin aqueous dispersion of bioadhesive moisturizing particles is also useful as a vaginal or rectal douche. A gel-like consistency is preferred for a vaginal moisturizer, with the composition being applied by means of a plunger-type applicator as is well known for use in applying vaginal products.

In another illustrative embodiment, the bioadhesive moisturizing agent is intimately mixed in a pharmaceutically acceptable aqueous carrier as diluent for use in an eye. The bioadhesive is preferably comminuted or otherwise sized to a number average size of about 2 to about 5 microns in the longest dimension for use in the eye. The composition so prepared can then be instilled as drops in the precorneal pocket of the eye to contact the conjunctival surface, and thereby provide contact of the moisturizing composition to that mucous membrane.

Best Modes For Carrying Out The Invention

EXAMPLE 1

Bioadhesive Polymer Preparation

Bioadhesive polymers useful herein were prepared following the general synthetic procedure discussed immediately below. Specific bioadhesive polymers made in accordance with the general procedure are illustrated in Table 1, hereinafter.

A solution containing 100 milliliters of distilled water and 800 grams of magnesium sulfate ($MgSO_4$-$7H_2O$) was heated to reflux with agitation. A mixture of 1 gram of initiator dissolved in 100 grams of monomeric carboxy-functional repeating unit and the amount of cross-linking agent shown in Table 1 was added to the refluxing aqueous solution with continued stirring. The polymerizing composition so prepared was agitated and heated to the temperature shown in Table 1 for the period of initial polymerization and of postpolymerization curing.

At the termination of the curing time, the polymerized composition was diluted with 150 milliliters of distilled water heated to a temperature of about 95 C. and then strained through a stainless steel sieve having a 40 mesh screen (U.S. Standard Sieve Series). The strained bioadhesive remaining on the screen was washed with one 1 liter portion of water heated to a temperature of about 80 C. followed by five separate 1 liter washings using tepid water. The washed bioadhesive so prepared was then dried in a forced air oven at a temperature of 90 C. for a period of 48 hours.

The bioadhesives so prepared were then used as such or comminuted and sieved to provide a desired particle size.

TABLE 1

| Bioadhesives | | | | | | |
|---|---|---|---|---|---|---|
| Carboxy-functional Repeating Unit[1] | Cross-Linking Agent[2] | Initiator[3] | Poly Time[4] | \multicolumn{3}{c}{Polymerization Conditions} |
| | | | | T[5] | Time[6] | Yield[7] |
| (A) | (a) 0.2 | (1) | 15 | 95 | 2 | 83 |
| (A) | (b) 1.0 | (1) | 25 | 95 | 18 | 67 |
| (B) | (a) 1.0 | (1) | 30 | 95 | 48 | 53 |
| (B) | (b) 1.0 | (1) | 30 | 95 | 48 | 87 |
| (C)[8] | (a) 1.0 | (1) | — | 65 | 24 | 11 |
| (D)[8] | (a) 0.2 | (2) | 20 | 95 | 72 | 10 |
| (A) | (c) 0.2 | (1) | 10 | 95 | 4 | 98 |
| (B) | (c) 0.2 | (1) | 10 | 95 | 20 | 93 |

[1]100 Grams of each of the following carboxy-functional repeating units was used: (A) = acrylic acid; (B) = methacrylic acid; (C) = itaconic acid; and (D) = amleic anhydride.
[2]The numerals of the Table indicate the number of grams of the particular cross-linking agent used. The particular cross-linking agents were: (a) = 3,4-dihydroxy-1,5-hexadiene; (b) = divinyl benzene; and (c) = 2,5-dimethyl-1,5-hexadiene.
[3]One gram of the following initiators was used: (1) = benzoyl peroxide; and (2) = azobisisobutyronitrile.
[4]Initial polymerization time in minutes.
[5]Temperature in degrees C. for initial polymerization and post-polymerization cure.
[6]Post-polymerization cure time in hours.
[7]Yield of dried bioadhesive based upon the weights of starting materials and recovered bioadhesive.
[8]A nitrogen sparge was used during polymerization as was deaerated distilled water prepared by boiling distilled water for a period of 10 minutes.

Although optimization of polymerization conditions is not reflected in the data of Table 1, it can be seen from those data that the bioadhesives useful herein are easily prepared in useful quantities. It is noted that the first bioadhesive listed in Table 1 has bioadhesion and other physical and chemical properties that are substantially identical to the commercially available bioadhesive sold under the designation polycarbophil by A. H. Robins Co. of Richmond, Va., as well as that sold under the designation EX55 by B. F. Goodrich Chemical Co. of Cleveland, Ohio.

EXAMPLE 2

Measurement of Adhesion

As noted previously, a bioadhesive moisturizing polymer of this invention is a water-insoluble, but water-swellable, particulate, fibrous, cross-linked carboxy-functional polymer that contains specified amounts of carboxyl functionality and crosslinking agent. In addition, to that chemical definition, a useful bioadhesive by definition must also exhibit an adhesion between two pieces of freshly excised rabbit stomach tissue of at least about 50 dynes/$cm^2$ when measured under specified conditions specified in Example 2 of U.S. Pat. No. 4,615,697.

Exemplary results using the above measurement technique are illustrated for four useful bioadhesives in Table 2 hereinafter. The bioadhesives were prepared as described in Example 1 with the exception that 0.3 weight percent of cross-linking agent was utilized. After the preparation, the bioadhesives were sieved and dry particles having a 30/40 mesh size (U.S. Standard Sieve Series) were used for these measurements.

TABLE 2

Bioadhesion Measurements

| Polymer[1] | Weight to Separate Tissues[2] | Force to Separate Tissues[3] | Number of Measurements |
|---|---|---|---|
| 1 | 855 ± 55 | 1061 ± 68 | 13 |
| 2 | 864 ± 56 | 1072 ± 68 | 12 |
| 3 | 876 ± 57 | 1086 ± 71 | 13 |
| 4 | 306 ± 45 | 380 ± 56 | 8 |

[1]Polymer 1 = polyacrylic acid cross-linked with 3,4-dihydroxy-1,5-hexadiene; polymer 2 = polyacrylic acid cross-linked with 2,5-dimethyl-1,5-hexadiene; polymer 3 = polyacrylic acid cross-linked with divinylbenzene; and polymer 4 = polymethacrylic acid cross-linked with divinylbenzene.
[2]Weights are in milligrams ± standard error of the mean (S.E.M.)
[3]Forces are reported in dynes/cm$^2$ ± S.E.M.

Using the above measuring technique, p-HEMA commercially available from Aldrich Chemical Co. of Milwaukee, Wis., required a force of 29 dynes/cm to separate the tissues, while AMBERLITE® 200 cationic exchange resin available from Rohm and Haas Co. of Philadelphia, Pa., required almost no force to separate the tissues.

EXAMPLE 3

Bioadhesion as a Function of pH Value

Figure 1:
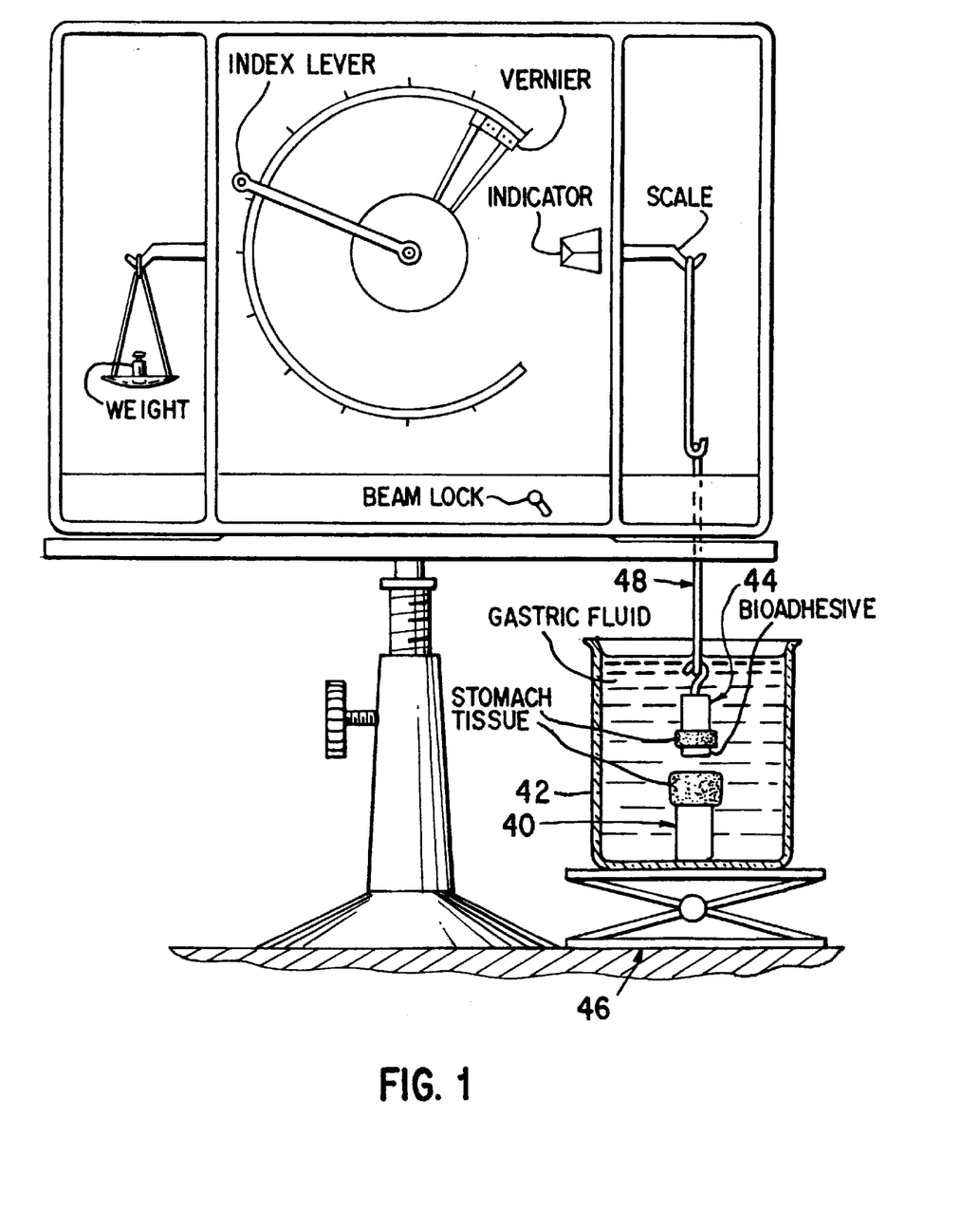
FIG. 1 illustrates a diagrammatic side view of a modified, commercially available surface tensiometer utilized to measure adhesive strength of bioadhesives.
Figure 2:
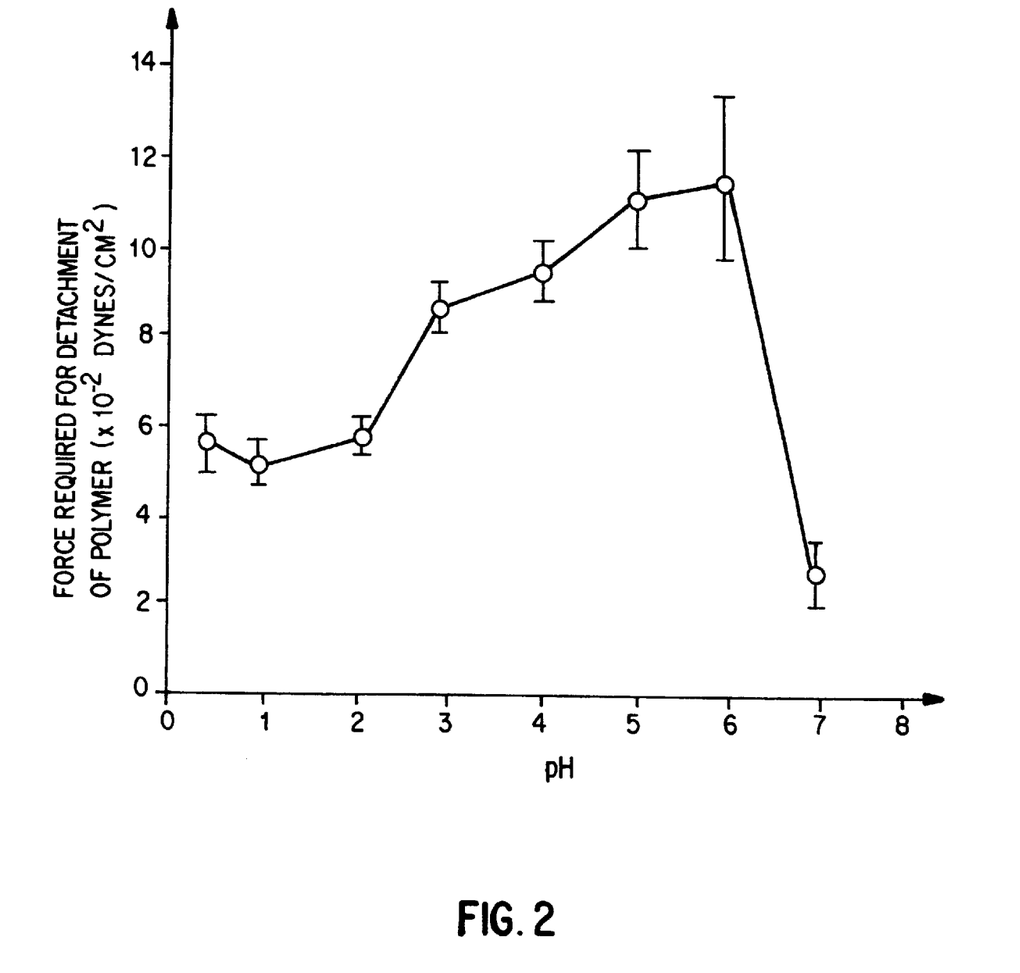
FIG. 2 is a graph illustrating the force (dynes×$10^{-2}$/cm$^2$) for detaching a bioadhesive polymer reaction product of acrylic acid copolymerized with 0.3 weight percent 3,4-dihydroxy-1, 5-hexadiene having a density of 1.56 grams/cubic centimeter (g/cc) versus pH value.

The force measured to separate a bioadhesive polymer that is the reaction product of the polymerization of acrylic acid with 0.3 weight percent of 3,4-dihydroxy-1,5-hexadiene that had a density of 1.56 g/cc is shown in FIG. 2. As is seen from the Figure, the maximum adhesion was observed at a pH value of about 5 to about 6. That maximum value was more than twice the adhesive force required for the separation at pH values of 0.46, 1.42 or 2.0. As is also seen, adhesion provided by that bioadhesive polymer was substantially reduced at pH value of 7. That reduction was statistically significant in a Student's t-test, p less than 0.01. Bioadhesive forces were measured as discussed previously in Example 2.

EXAMPLE 4

Method of Moisturizing Dry Vagina

A moisturizing composition containing dry polycarbophil (20 g, B. F. Goodrich EX55) sized to pass through a 400 mesh sieve screen (U.S. Standard Sieve Series) and whose number average longest dimensions are less than about 20 microns, CARBOPOL® 934 (10 g; B. F. Goodrich), a hydrogenated palm oil glyceride dispersant [10 g, MYVEROL 18-04K (Eastman)], heavy mineral oil (U.S.P. heavy; 50 ml, Purepac), glycerin U.S.P. (100 ml, Purepac), methyl paraben (1.0 g) and distilled, deionized water up to 1000 g was prepared by admixing with agitation as an emulsion. The pH value was adjusted to pH 2.4 with a solution of sodium citrate in HCl.

About 4 g of the above composition are placed into a plunger-type applicator. The applicator and its contents are placed into the vagina of a post-menopausal woman presenting with dry vagina and vaginitis, and the plunger is depressed to expel the composition into the subject's vaginal cavity to thereby contact the vaginal mucosa. The composition so applied moisturizes the mucosa and also provides lubrication for sexual intercourse.

EXAMPLE 5

Comparative Viscosity Study

Three aqueous vaginal moisturizing compositions substantially identical to the composition of Example 4 were prepared, but in which the amounts of polycarbophil as bioadhesive moisturizing polymer was varied and CARBOPOL® 934 as consistency-enhancing agent was held constant, with more or less water being used to complete the composition.

All three compositions contained 1 weight percent CARBOPOL® 934. Composition 1 contained 1 weight percent of polycarbophil. Composition 2, like that of Example 4, contained 2 weight percent polycarbophil, whereas Composition 3 contained 3 weight percent polycarbophil. Composition 1 was deemed too thin for use although it had a creamy consistency. Composition 3 was too thick for dispensing. Composition 2 had an appropriate viscosity for dispensing with a plunger-type apparatus and exhibited a good feel when rubbed on the skin.

EXAMPLE 6

Viscosity Measurements

A moisturizing composition of the present invention is viscous, preferably having a gel-like consistency that is somewhat thicker or more viscous than mayonnaise. Such a composition exhibits non-Newtonian flow characteristics that can be described as thixotropic; i.e., the flow is characterized by 1) a yield point, 2) pseudoplastic behavior, 3) a reduction in viscosity on continued shearing, visible over a finite time, and 4) a tendency to rebuild viscosity and/or yield point on standing.

Because of the non-Newtonian character of a contemplated moisturizing composition, viscosity measurements are made in a viscometer that is especially designed for such fluids. Viscosity values are therefore reported at a noted temperature and shear rate, using a particular viscosimeter.

The viscometer utilized for the viscosity measurements discussed herein is a commercially available Haake ROTOVISCO Model RV-12, available from Haake, Inc., 244 Saddle Brook Road, Saddle Brook, N.J. 07662. The machine utilized an SV cup and an SVII rotor for determining viscosity in centipoises (cps) at shear rates of 1–8 revolutions per minute (rpm) and at a temperature of 25 degrees C.

Two exemplary moisturizing compositions prepared as discussed in Example 4 were made separately, by different persons. The viscosities of both compositions were separately measured at shearing rates of 1, 2, 4 and 8 rpm, and then compared.

Figure 3:
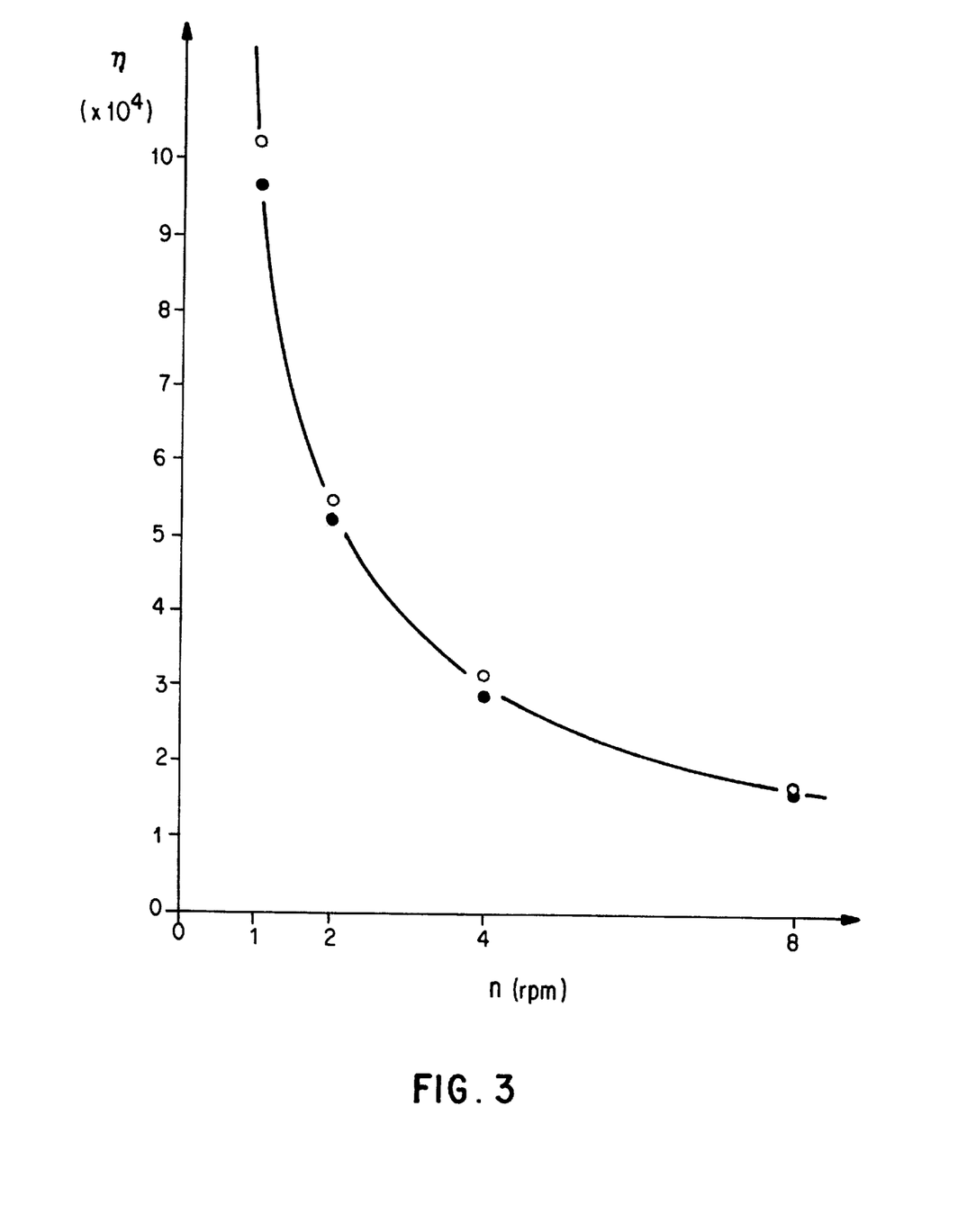
FIG. 3 is a graph of viscosity, n, in cps from 10,000–100,000, shown for convenience as 1–10×$10^4$, versus shear rate, n, in rpm for two separately made moisturizing compositions prepared as described in Example 4. The results were obtained using a Haake ROTOVISCO Model RV-12 viscometer as discussed in Example 6, and data for one composition are shown in closed circles, whereas data for the other are shown in open circles.

The results of this comparison are illustrated in FIG. 3 in which viscosity, n, in cps ×10$^4$ is plotted against the shearing rate, n, in rpm. Open and closed circles are utilized to show datum points for one or the other of the compositions.

EXAMPLE 7

Comparative Vaginal Moisturization

A double-blind study of vaginal moisturization was conducted under the guidance of qualified physicians using a moisturizing composition and method of this invention (Example 4) and a commercially available vaginal lubricating product that is described by its manufacturer as a greaseless, water-soluble jelly which is clear, spreads easily and is non-irritating. A total of 89 peri- and postmenopausal women were enrolled in the study. A total of eight subjects withdrew from the study for various reasons.

A complete medical history and a physical examination were carried out for each enrollee prior to beginning the study. A vaginal examination was conducted and a PAP smear taken for vaginal cytology. A vaginal dryness index determination was made, including a measurement of the pH value.

A fixed dose of 2.5 grams of either composition was inserted nightly into the vagina of an enrollee for five consecutive days. No composition was administered on days 6 through 8.

Vaginal dryness indices, vaginal pH values and PAP smears were determined on days 5 through 8. The enrollees used the other composition on days 9 through 13 and the above data were again recorded on days 13 through 16. Enrollees were also asked to keep diaries during the study period, were told to maintain their usual sexual habits during the time of the study, and were instructed to use no vaginal medications, including douches, during the study.

A majority of the enrollees (57.5 percent) had used vaginal lubricants previously, with the majority (71.4 percent) reporting vaginal pain as the reason for that use. Vaginal dryness was reported as a constant in 37.6 percent of the enrollees, episodic in 31.8 percent, and had started episodic but was now constant in 30.6 percent. Results were determined using statistical methods.

The results of this study can be summarized as follows:

(1) There was a statistically significant decrease (at the 0.01 level) of vaginal pH when a composition of this invention was used, but no decrease in pH value when the commercially available jelly was used. The vaginal pH value remained at about pH 5 or below for approximately 48 hours after the last administration of the composition.

(2) The moisturizing effect of the gel composition of this invention tended to last longer than when the commercial product was used ($p<0.001$). Moisturization lasting longer than 12 hours was reported for more enrollees who used the gel of this invention, whereas a less than 6 hour duration was more frequently reported with the commercial product jelly.

(3) When asked which composition they preferred, 61.5 percent favored the composition of this invention, whereas 25.6 percent favored the commercial jelly.

(4) Vulvar moisturization was present or partial in most women receiving the gel composition of this invention. More enrollees reported leakage with the commercial lubricating jelly than with a composition of this invention. None of the enrollees reported too much vulvar moisturization with the gel of this invention, whereas 40 percent reported too much vulvar moisturization when using the commercial lubricating jelly.

(5) Ten women reported their condition to be worse using the commercial lubricating jelly compared to one woman using the gel of this invention. Five women reported their conditions to be worse on both compositions. No residue was reported by women using the water-soluble commercial lubricating jelly compared to 7.8 percent making such a report when using the gel of this invention.

(6) Mucosa were ranked higher when using the gel of this invention compared to the commercial jelly. The difference between use of the two compositions was not statistically significant although there was a statistically significant difference between use of the gel composition and the pretreatment control value.

(7) Moisture levels were statistically significantly higher using the gel composition of this invention as compared to both the control value and the value using the commercially available lubricating jelly.

The Vaginal Dryness Index assessed five parameters, giving each a numerical score of 1–5, with 5 being the best. Thus, the lower the score, the greater is the lack of vaginal lubrication.

The five parameters and their scoring (in parenthesis) were as follows:

1. Overall Vaginal Elasticity
   (1) none, (2) poor, (3) fair, (4) good, (5) excellent;
2. Vaginal Secretion Type & Consistency
   (1) none, (2) scant thin yellow, (3) superficial layer of thin white, (4) moderate layer of thin white, (5) normal [white flocculent];
3. pH Value
   (1) 6.1 or above, (2) 5.6–6.0, (3) 5.1–5.5, (4) 4.7–5.0, (5) 4.6 or below;
4. Vaginal Mucosa
   (1) petechiae noted before contact, (2) 10 bleeds with high contact, (3) bleeds with scraping, (4) not friable-thin mucosa, (5) not friable normal mucosa; and
5. Vaginal Moisture
   (1) none, mucosa inflamed, (2) none, 15 mucosa not inflamed, (3) minimal, (4) moderate, (5) normal.

EXAMPLE 8

Method of Moisturizing Dry Skin

A composition of dry polycarbophil (5 g, B. F. Goodrich EX55) sized to pass through a 400 mesh sieve screen (U.S. Standard Sieve Series) and whose number average longest dimensions are less than about 20 microns, micro-silicate particles (3.75 g Syloid 244 FP, Davison Chemical Division, W. R. Grace & Co., Baltimore, Md.), light mineral oil (50 ml), 95 ethanol (250 ml) and water (q.s. ad distilled deionized water 1000 ml) is prepared by admixture with agitation.

The composition so prepared is spread upon the dry skin surface in an amount of about 0.5–1 g per 20–30 $cm^2$ of skin to be moisturized, and allowed to adhere. The polymer composition adheres to the contact area and holds water in contact with the dry skin surface.

EXAMPLE 9

Method of Moisturizing Dry Skin

A composition is prepared by admixing with agitation dry polycarbophil (5.00 g; B. F. Goodrich EX55) having a number average particle size of about 2 to about 5 microns and CARBOPOLOL® 934P (2.50 g), Syloid 244 FP (3.75 g) with light mineral oil (50.00 ml), 95% ethanol (250.00 ml), urea (100.00 g), methylparaben (1 g), propylparaben (0.5 g) and diluted to 1000 ml with distilled, deionized water. The resulting composition has a smooth creamy texture.

This composition is utilized as described above in Example 4 for treating dry skin. The presence of the mineral oil and CARBOPOL® 934 in the composition improve its texture and make the composition more lubrous when applied to the skin.

EXAMPLE 10

Method of Moisturizing Dry Vagina

A composition prepared from the dry polycarbophil (3 g) of Example 8, methyl paraben (0.2 g), propylparaben (0.03 g) and water (100 ml) is admixed and agitated, and adjusted to pH 2.4 with a solution of sodium citrate in HCl. The composition so prepared has a gel-like consistency.

About 4 g of the above composition are placed into a plunger-type applicator. The applicator and its contents are placed into the vagina of a postmenopausal woman presenting with dry vagina and vaginitis, and the plunger is depressed to expel the composition into the subject's vaginal cavity to thereby contact the vaginal epithelia. The composition so applied moisturizes the mucosa and also provides lubrication for sexual intercourse.

EXAMPLE 11

Method for Moisturizing Dry Mouth

A composition prepared from the dry polycarbophil (2.0 g), of Example 8, sorbitol [NEOSORB® P100T (10 g, Roquette Corporation)], aspartame (6 g, NUTRASWEET®), lemon-vanilla flavoring (1.0 g), methylparaben (0.20 gm), propylparaben (0.03 g) and water (100 ml) is prepared by admixture and agitation, and adjusted to pH 2.3 with sodium citrate-HCl in HCl.

The composition is administered into the mouth to moisturize dry or desiccated tissue therein. A similar composition can be administered in several application forms, such as an aqueous spray, a gel, a chewable tablet, a dry powder, wafer, pastille, lozenge and an emulsion. The additional application forms are prepared by well known techniques and need only contain the bioadhesive moisturizing polymer of the abovelisted ingredients.

Regardless of the form in which the composition is used, the bioadhesive polymer contacts the buccal membranous tissue and maintains water within the oral mucosa.

EXAMPLE 12

Method of Moisturizing Dry Eye

Polycarbophil (B. F. Goodrich EX55) is dried, crushed and sieved to provide particles that pass through a 400 mesh sieve screen (U.S. Standard Sieve Series), and whose number average longest dimension is about 2–5 microns. A composition of those particles of polycarbophil (3.0 g) and water (100 ml) is prepared by admixture with agitation, and adjusted to about pH 5.5. An electrolyte is added with further agitation to provide a thickened liquid. That liquid is applied to the ophthalmic epithelia in an amount of about 0.025–0.05 ml with an eye dropper. The resulting contact with the ophthalmic mucosa is maintained until the treated subject requires another treatment as is evidenced by itching of the eye.

The foregoing is intended as illustrative of the present invention but not limiting. Numerous variations and modifications may be effected without departing from the true spirit and scope of the novel concepts of the invention.

I claim:

1. A method of moisturizing mammalian epithelial cells comprising:

(a) contacting mammalian epithelial cells to be moisturized with an effective moisturizing amount of an aqueous composition, which is free of a treating agent, comprising water and a moisturizing amount of a bioadhesive moisturizing polymer having an adhesive force of at least about 380 dynes per square centimeter, said bioadhesive moisturizing polymer comprising a water-swellable, but water-insoluble, cross-linked caboxy-functional polymer; and (b) maintaining said contact for a time period sufficient to moisturize said contacted epithelial cells.

2. An epithelial tissue moisturizing composition, which is free of a treating agent, comprising water and a moisturizing amount of a bioadhesive moisturizing polymer having an adhesive force of at least about 380 dynes per square centimeter, said bioadhesive moisturizing polymer comprising particles of a water-swellable, but water-insoluble, cross-linked carboxy-functional polymer in free acid form.

3. An epithelial tissue moisturizing composition, which is free of a treating agent, comprising water and a moisturizing amount of a bioadhesive moisturizing polymer having an adhesive force of at least about 380 dynes per square centimeter, said bioadhesive moisturizing polymer consisting essentially of particles of a water-swellable, but water-insoluble, cross-linked carboxy-finctional polymer consisting essentially of (a) a plurality of repeating units which contain at least one carboxyl functionality in its free acid form, and (b) about 0.01 to about 6 percent cross-linking agent, said percentages being based upon the weights of unpolymerized repeating units and cross-linking agent, respectively.

4. The method according to claim 1 wherein said bioadhesive polymer consists essentially of repeating units essentially all of which contain at least one carboxyl functionality in its free acid form.

5. The method according to claim 4 wherein said bioadhesive polymer contains about 0.01 to about 6 percent cross-linking agent.

6. The method according to claim 5 wherein said cross-linking agent is substantially free from polyalkenyl polyether.

7. The composition according to claim 2 wherein said bioadhesive polymer contains a plurality of repeating units of which essentially all contain at least one carboxyl functionality.

8. The composition according to claim 7 wherein said bioadhesive polymer contains about 0.01 to about 6 percent cross-linking agent.

9. The composition according to claim 8 wherein said cross-linking agent is substantially free from polyalkenyl polyether.

10. The composition according to claim 2 wherein said bioadhesive polymer contains a plurality of repeating units essentially all of which contain at least one carboxyl functionality in its free acid form.

11. The composition according to claim 10 wherein said bioadhesive polymer contains about 0.01 to about 6 percent cross-linking agent.

12. The composition according to claim 11 wherein said cross-linking agent is substantially free from polyalkenyl polyether.

* * * * *